(12) United States Patent
Mansour et al.

(10) Patent No.: US 10,457,967 B2
(45) Date of Patent: Oct. 29, 2019

(54) IN-SITU BIOSTIMULATION OF THE HYDROLYSIS OF ORGANIC MATTER FOR OPTIMIZING THE ENERGY RECOVERY THEREFROM

(71) Applicant: VEOLIA ENVIRONNEMENT VE, Paris (FR)

(72) Inventors: Alicia Mansour, Mantes la Jolie (FR); Jesùs Andrés Cacho Rivero, Mantes la Jolie (FR); Maria Fdz-Polanco Iñiguez De La Torre, Valladolid (ES)

(73) Assignee: VEOLIA ENVIRONMENT—VE, Paris (FR)

( * ) Notice: Subject to any disclaimer, the term of this patent is extended or adjusted under 35 U.S.C. 154(b) by 56 days.

(21) Appl. No.: 15/537,800

(22) PCT Filed: Dec. 17, 2015

(86) PCT No.: PCT/FR2015/053603
§ 371 (c)(1),
(2) Date: Jun. 19, 2017

(87) PCT Pub. No.: WO2016/097638
PCT Pub. Date: Jun. 23, 2016

(65) Prior Publication Data
US 2018/0023106 A1    Jan. 25, 2018

(30) Foreign Application Priority Data
Dec. 18, 2014    (FR) ........................................ 14 62722

(51) Int. Cl.
*C12P 19/14*    (2006.01)
*C05F 17/00*    (2006.01)
(Continued)

(52) U.S. Cl.
CPC ............ *C12P 19/14* (2013.01); *B09B 3/0016* (2013.01); *B09B 5/00* (2013.01); *C05F 17/0027* (2013.01); *C12P 5/023* (2013.01); *C12P 19/02* (2013.01); *C12Y 302/01004* (2013.01); *C12Y 302/01021* (2013.01); *C12P 21/00* (2013.01);
(Continued)

(58) Field of Classification Search
CPC ..... B09B 3/0016; B09B 5/00; C05F 17/0027; C12P 19/02; C12P 19/14; C12P 21/00; C12P 2201/00; C12P 5/023; C12P 39/00; C12P 5/02; C12Y 302/01021; C12Y 302/01004; Y02E 50/343; Y02E 20/12; Y02E 50/14; Y02E 50/15; Y02E 50/32; Y02P 20/145; Y02P 20/582; Y02P 20/59; Y02P 20/143; Y02P 30/20; Y02P 30/20; Y02W 30/43; Y02W 30/47; Y02W 10/15; Y02W 10/37; C10B 1/10; C10B 47/30; C10B 49/14; C10B 49/16; C10B 53/02; C10B 53/07; C10C 5/00; C10G 1/02; C10G 2300/1007; C10G 2300/1011; C10G 2300/1014; C10G 2300/1022; C10G 2/30; C10L 9/083; F23G 2203/209; F23G 2900/50801; F23G 5/20; F27B 7/02; F27B 7/3205; F27B 7/33; B09C 1/10; B09C 1/085; C12Q 1/6837; C12Q 2537/165; C12Q 1/689; C12Q 2600/158; C12N 11/16; C12N 1/20; C12N 9/14; C12N 1/04; C12N 1/38; A61B 10/02; A61B 17/22012; A61B 17/3403; A61B 18/24; A61B 18/245; A61B 1/0051; A61B 1/0056; A61B 2017/00039; A61B 2017/00106; A61B 2017/00243; A61B 2017/00247; A61B 2017/003; A61B 2017/00867; A61B 2017/22002; A61B 2017/22008; A61B 2018/00392; A61B 2018/2211; A61B 2018/2272; A61B 2034/2051; A61B 2090/363; A61B 2090/374; A61B 2090/378; A61B 2090/3954; A61B 34/20; A61B 5/0422; A61B 5/06; A61B 5/061; A61B 5/6885; A61B 8/0833; A61B 8/0841; A61B 8/12; A61M 2025/0166; A61M 25/01; A61M 25/0105; A61M 25/104; A61N 1/05; A61N 2005/0659; A61N 5/0601; A61N 5/062; C02F 2101/36; C02F 2103/06; C02F 3/025; C02F 3/06; C02F 3/10; C02F 3/34; C02F 3/341; A62D 2101/22; A62D 3/02;
(Continued)

(56) References Cited

U.S. PATENT DOCUMENTS

2009/0229179 A1* 9/2009 Hafeel ................... A01G 2/00
47/58.1 SC
2015/0237807 A1* 8/2015 Valiquette ............. A01G 22/00
47/66.7

FOREIGN PATENT DOCUMENTS

WO    WO2004/113490 A2    12/2004
WO    WO2014/113490 A3    12/2004
WO    WO2013/163703 A1    11/2013

OTHER PUBLICATIONS

Khokhar, Z.-U., et al., "On-site cellulase production by Trichoderma reesei 3EMS35 mutant and same vessel saccharification and fermentation of acid treated wheat straw for ethanol production," Excli Journal 2014;13:82-97.
(Continued)

*Primary Examiner* — Deborah K Ware
(74) *Attorney, Agent, or Firm* — Kenealy Vaidya LLP

(57) ABSTRACT

Some embodiments are directed to a process for the treatment of organic waste which couples in situ biostimulation to produce hydrolytic enzymes and hydrolysis of the refractory organic matter from waste using these enzymes with a view to energy recovery.

16 Claims, 4 Drawing Sheets

(51) Int. Cl.
*C12P 19/02* (2006.01)
*C12P 5/02* (2006.01)
*B09B 3/00* (2006.01)
*B09B 5/00* (2006.01)
*C12P 21/00* (2006.01)

(52) U.S. Cl.
CPC .......... *C12P 2201/00* (2013.01); *Y02E 50/343* (2013.01); *Y02P 20/145* (2015.11); *Y02P 20/582* (2015.11); *Y02P 20/59* (2015.11); *Y02W 30/20* (2015.05); *Y02W 30/43* (2015.05); *Y02W 30/47* (2015.05)

(58) Field of Classification Search
CPC .......... B01D 53/84; C09K 8/582; C12R 1/01; E21B 43/16; Y02A 50/2358
See application file for complete search history.

(56) References Cited

OTHER PUBLICATIONS

Koutinas, A. A., et al., "Cereal-based biorefinery development: Integrated enzyme production for cereal flour hydrolysis," Biotechnol. Bioeng. 2007;97(1):61-72.

Pirota, E. D. P. B., et al., "Simplification of the Biomass to Ethanol Conversion Process by Using the Whole Medium of Filamentous Fungi Cultivated Under Solid-State Fermentation," Bioenergy Res. 2014;7(2):744-752.

International Search Report for PCT Patent App. No. PCT/FR2015/053603 dated Mar. 10, 2016 with partial English language translation.

Written Opinion for PCT Patent App. No. PCT/FR2015/053603 dated Mar. 10, 2016.

* cited by examiner

IN-SITU BIOSTIMULATION OF THE HYDROLYSIS OF ORGANIC MATTER FOR OPTIMIZING THE ENERGY RECOVERY THEREFROM

CROSS REFERENCE TO RELATED APPLICATIONS

This application is a National Phase filing under 35 C.F.R. § 371 of and claims priority to PCT Patent Application No.: PCT/FR2015/053603, filed on Dec. 17, 2015, which claims the priority benefit under 35 U.S.C. § 119 of French Application No.: 1462722, filed on Dec. 18, 2014, the contents of which are hereby incorporated in their entireties by reference.

BACKGROUND

Some embodiments relate generally to the field of biological treatments and the exploitation of organic waste.

More particularly, some embodiments relate to a process for the treatment of organic waste which couples in situ biostimulation to produce hydrolytic enzymes and hydrolysis of the refractory organic matter from waste using these enzymes with a view to energy recovery.

Hydrolysis corresponds to a step in solid-state fermentation which promotes the growth of different types of microorganisms, inter alia filamentous fungi, which produce extracellular hydrolyzing enzymes. The production of enzymes by solid-state fermentation is a process known to those skilled in the art and well documented in the scientific literature[1,2,3].

Moreover, patents and patent applications describing the production of enzymes in solid medium are also found in the literature. More particularly, the Malaysian patent application MY142205, "Solid-state bioconversion of oil palm biomass by white rot fungus for ligninase production in rotary drum bioreactor" describes the use of *Phanerochaete chrysosporium* for producing ligninase. A substrate (or solid organic waste) is prepared (delignified) before solid-state fermentation and then the enzyme produced is collected. International application WO 2013/114282 ("Reduction of non-starch polysaccharides and alpha-galactosides in soy-flour by means of solid-state fermentation using cellulolytic bacteria isolated from different environments" describes a process for solid-state fermentation of soy flour in the solid state, in which cellulolytic bacteria are inoculated in the medium. Finally, international application WO 2013/162165 ("Method for producing large quantities of cellulase using palm by-products") describes a process for solid-state fermentation using the fungus *Aspergillus oryzea* to produce cellulase.

The drawback of these processes of solid-state fermentation lies in the fact that the phase of preparing the solid matrix must allow for a very fine particle size, which is not possible in industrial installations. Other types of preparation of the matrix also involve chemical pretreatments for delignification or physical pretreatments such as sterilization and autoclaving. There is also the constraint of preparing the inoculum.

Moreover, it is known to those with ordinary skill in the art to use enzymes to degrade the organic matter. Thus, in the scientific literature a certain number of articles are found, describing processes of solid-state fermentation for producing different types of enzymes, which are extracted and used in tests of production of reducing sugars on various matrices (referred to as saccharification assays)[4,5,6,7]. Likewise, the Russian patent RU2238319 ("Complex enzyme preparation for hydrolysis of vegetable waste, among them food waste") describes the use of enzymes (mixture of enzymes) to degrade the organic matter.

American patent U.S. Pat. No. 7,270,751 ("Method for treatment of sewage plant sludges by a fungal process") and the American patent application US 2013/0040354 ("Biogas production process with enzyme pre-treatment") and the international patent applications WO 2010/000858 ("A personal wash bar") and WO 2013/163703 ("Integrated process for producing enzyme formulations from agro-industrial waste and biofuel production") more specifically describe enzymatic hydrolysis and the degradation of organic matter:

U.S. Pat. No. 7,270,751 describes a process for treating municipal sludge by fungi, which comprises a step of oxidation, then a step of addition of antibiotics and of oxidizing compounds and finally a step of injection of a microfungus into the system to perform the treatment;

in US 2013/0040354 and WO 2010/000858, physical/chemical/biological pretreatments are used and followed by addition of external enzymes and finally by a fermentation step;

WO 2013/163703 describes the production of a specific enzyme formula by solid-state fermentation, which is then extracted and used for the production of bioethanol or other products of green chemistry.

SUMMARY

Thus, the known processes of the prior art use enzymes as a solution for the hydrolysis of refractory organic matter. However, these enzymes are produced, extracted and used following processes involving a sequence of complex steps, which involves a high cost, especially as regards the phase of separation and filtration of the liquid medium (to recover the enzymes). In certain cases, commercial enzymes are added to the medium; however, this involves significant costs, which are sometimes prohibitive for environmental applications. These various processes are costly and do not necessarily make it possible to treat a complex substrate.

Within the meaning of the present invention, substrate is intended to mean, without distinction, any type of waste including at least one organic portion: household waste, green waste or industrial waste, paper, cardboard, or biomass. The substrates are usually in solid form or comprise at least one solid portion.

Within the meaning of the present invention, complex substrate is intended to mean waste of various origins containing refractory organic matter. The complex substrate may be in solid or liquid form.

Some embodiments addresses or overcome all or some of the drawbacks of the prior art, by carrying out a process for treating solid organic waste which couples in situ biostimulation to produce hydrolytic enzymes from a substrate, and hydrolysis of the refractory organic matter from the waste to be treated using these enzymes. The use of these enzymes produced in situ from waste (substrate) is more effective because it is better adapted to the waste to be treated.

Within the meaning of the present invention, biostimulation is intended to mean the stimulation of the degradation of organic waste by indigenous microorganisms. Biostimulation is a biological technique which does not require the addition of specific selected microorganisms. Unlike bioaugmentation, which consists in inoculating exogenous strains, biostimulation is the act of promoting the growth of strains of microorganisms which are already present in a given medium.

Using a complex solid medium enables a varied production of enzymes which will enable a better hydrolysis of the substrate that it is desired to treat due to its complex composition. Indeed, the substrate intended to be treated comprises different compounds which require a mixture of enzymes in order to obtain optimal hydrolysis of the refractory organic matter. This makes it possible to increase the performance of the anaerobic process and hence the production of energy. Finally, in situ production of the enzymes used for the hydrolysis of the waste to be treated makes it possible to simplify the treatment process and considerably reduce the operating costs thereof.

More particularly, Some embodiments are directed to a process for the treatment of a first, at least partially organic and at least partially solid, substrate, including the following steps:
  A. introduction of an initial volume of the first substrate to be treated into at least one hydrolysis reactor;
  B. introduction of an initial volume of second substrate into at least one biostimulation reactor;
  C. biostimulation of the second substrate contained in the biostimulation reactor, under aerobic conditions, at a temperature of between 20° C. and 40° C., a pH of between 4 and 7, a moisture level of between 50% and 80% and a residence time of between 1 and 5 days, to ensure at least partial hydrolysis of the organic portion of said substrate and the in situ production of hydrolytic enzymes;
  D. percolation of a liquid through the volume of second substrate contained in the biostimulation reactor, in order to form a first leachate enriched in hydrolytic enzymes;
  E. injection of the first leachate enriched in hydrolytic enzymes into at least one hydrolysis reactor containing the first substrate to be treated;
  F. hydrolysis of the first substrate at least partially by the first enriched leachate;
the succession of the steps C and D defining a biostimulation cycle.

The first and second substrates may be identical or different.

Within the context of the present invention, the enzymatic production is carried out in solid medium, therefore in a different environment from that of the current large-scale production of enzymes which is carried out in liquid medium. Therefore, production in solid medium, whether the substrates are identical or different, is more advantageous than the current production methods.

If the substrates are identical, the enzymatic mixture produced may be more targeted. Nonetheless, this is not always the case, and this depends on the nature of the substrates used.

The hydrolytic enzymes used for the hydrolysis of the substrate to be treated (or first substrate) are produced by biostimulation of the second substrate contained in the biostimulation reactor, in aerobic medium (step C).

The conditions enabling this biostimulation have been defined for all the substrates which can be used within the context of this invention in order to extract hydrolytic enzymes therefrom. These conditions are within the ranges defined below for each of the following parameters:
  temperature: between 20° C. and 40° C.,
  pH: between 4 and 7,
  moisture level: between 50% and 80%, and
  residence time (in the biostimulation reactor): between 1 and 5 days.

Controls of pH, temperature and moisture are necessary in order to have good growth of the hydrolytic microorganisms, especially the mycelia of the filamentous fungi from which the hydrolytic enzymes may be produced.

These filamentous fungi may advantageously belong to the group consisting of the fungi *Trichoderma* sp., *Aspergillus* sp., *Pleurotus* sp., *Penicillium* sp., and *Fomitopsis* sp.

The hydrolytic enzymes produced in this way are extracted by percolation (step D) of a liquid through the volume of second substrate in order to form a first leachate enriched in hydrolytic enzymes.

The liquid used for the percolation through the volume of the second substrate may be fresh water or a recycled leachate treated by methanogenesis or by anaerobic digestion, which may advantageously be aerated before use.

The succession of the steps C and D may be repeated until the initial volume of second substrate in the biostimulation reactor is exhausted. Within the context of the present invention, it will be decided to carry out this succession of steps C and D as a function, on the one hand, of the performance of the process according to the invention and on the other hand of the operational costs linked to installation of a new substrate, while ensuring a balance is maintained between these two constraints.

Within the meaning of the present invention, exhausting a substrate is intended to mean that the hydrolyzable organic matter of this substrate has in large part been hydrolyzed.

Moreover, a substrate, the organic matter of which has in large part been hydrolyzed, has the advantage that post-treatment thereof will be limited.

Typically, the second substrate may be used for 3 to 5 cycles of biostimulation.

When the initial volume of second substrate is exhausted, it is advantageously possible to introduce a new volume of second substrate into the biostimulation reactor (additional step G).

Once the second substrate is exhausted, it may advantageously be treated by an aerobic treatment to obtain a stabilized compost.

Moreover, after formation by biostimulation of a first leachate enriched in hydrolytic enzymes, this is injected into at least one hydrolysis reactor containing the first substrate to be treated (step E), then the substrate to be treated is hydrolyzed by at least a portion of this first leachate (step F).

According to a first embodiment of the process according to the invention, the step F of hydrolysis of the first substrate to be treated may essentially occur in the solid phase.

Advantageously, the hydrolysis step F may occur in a percolator and comprise the following steps:
  step of percolation of the first leachate through the substrate to be treated in the percolator, in order to obtain a second leachate enriched in hydrolytic enzymes and in hydrolyzed organic matter; and
  step of reinjection of the second leachate into the percolator until the substrate to be treated (or first substrate) is exhausted, that is to say until the hydrolyzable organic matter of the first substrate has in large part been hydrolyzed.

When the initial volume of first substrate in the percolator is exhausted, it is advantageously possible to introduce a new volume of first substrate into the biostimulation reactor (additional step H).

In the same way as for the second substrate, once the first substrate is exhausted, the latter may advantageously be treated by aerobic treatment in order to obtain a stabilized compost.

According to a second embodiment of the process according to the invention, the hydrolysis step F of the first substrate to be treated may essentially occur in the liquid phase in a hydrolytic reactor.

At the end of the step F of hydrolysis of the first substrate by the first leachate, the products resulting from the hydrolysis step F may be exploited by a downstream step of methanogenesis in a methanizer, at the end of which treated water is obtained.

According to a third embodiment of the process according to the invention, the hydrolysis step F may be carried out in an anaerobic digestion reactor for the treatment of the first substrate and the production of biogas, at the end of which treated water is obtained.

Advantageously, the treated water resulting from the methanizer or the anaerobic digester may be used as percolating liquid during the step D of biostimulation in the biostimulation reactor, in order to extract hydrolytic enzymes therefrom. This treated wastewater may advantageously be aerated before being recycled to be injected into said biostimulation reactor.

Regardless of the embodiment envisaged, the first leachate enriched in hydrolytic enzymes may result from a single biostimulation reactor and supply a plurality of hydrolysis reactors.

Regardless of the embodiment envisaged, the step F of hydrolysis of the first substrate may occur over several biostimulation cycles, as a function especially of the nature of the substrate to be treated.

BRIEF DESCRIPTION OF THE DRAWINGS

Other advantages and particular features of the present invention will emerge from the following description, given by way of nonlimiting example and made in reference to the appended figures.

DETAILED DESCRIPTION

Identical elements represented in FIGS. 1 to 5 are identified by identical numerical references.

Figure 1A:
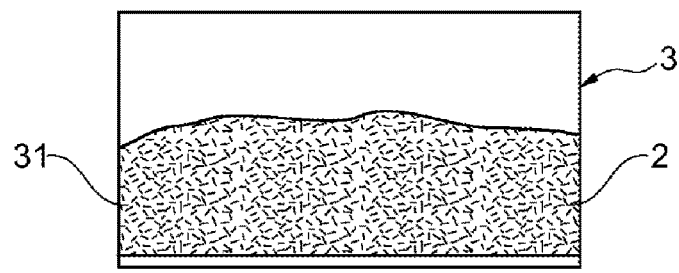
FIG. 1A represents a schematic diagram of a biostimulation reactor 3 during step C of biostimulation of a substrate 2 in order to extract hydrolytic enzymes 31 therefrom.
Figure 1B:
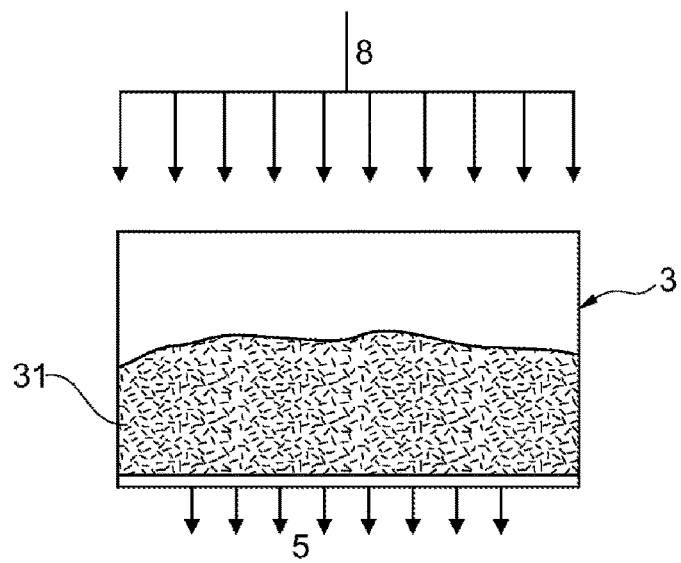
FIG. 1B represents a schematic diagram of the biostimulation reactor 3 of FIG. 1A during step D of percolation of a liquid through the substrate of FIG. 1A.
Figure 1C:
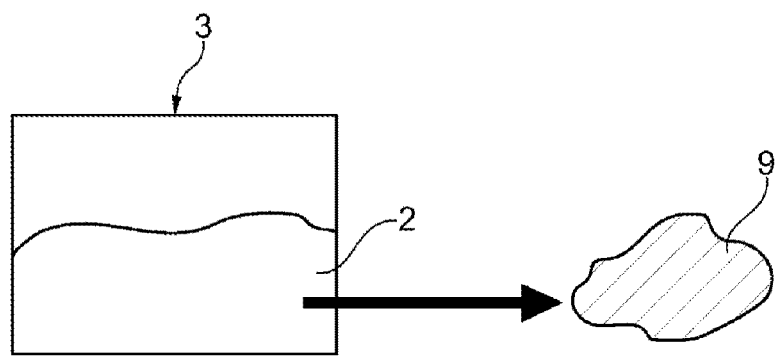
FIG. 1C represents a schematic diagram of the biostimulation reactor 3 of FIGS. 1A and 1B for the aerobic treatment of the exhausted substrate in order to obtain a stabilized compost.

In FIGS. 1A to 1C a biostimulation reactor 3 is represented, in which the biostimulation cycle of a substrate 2 occurs (second substrate which is not the substrate to be treated 1, but which may be identical to or different from this substrate 1).

FIG. 1A illustrates the step C of biostimulation in aerobic medium of a substrate 2 for producing hydrolytic enzymes 31, according to the following operation conditions:
- temperature: between 20° C. and 40° C.,
- pH: between 4 and 7,
- moisture level: between 50% and 80%, and
- residence time (in the biostimulation reactor): between 1 and 5 days.

Outside these operating ranges, the biostimulation of the substrate is possible but it does not have very good performance.

Figure 5:
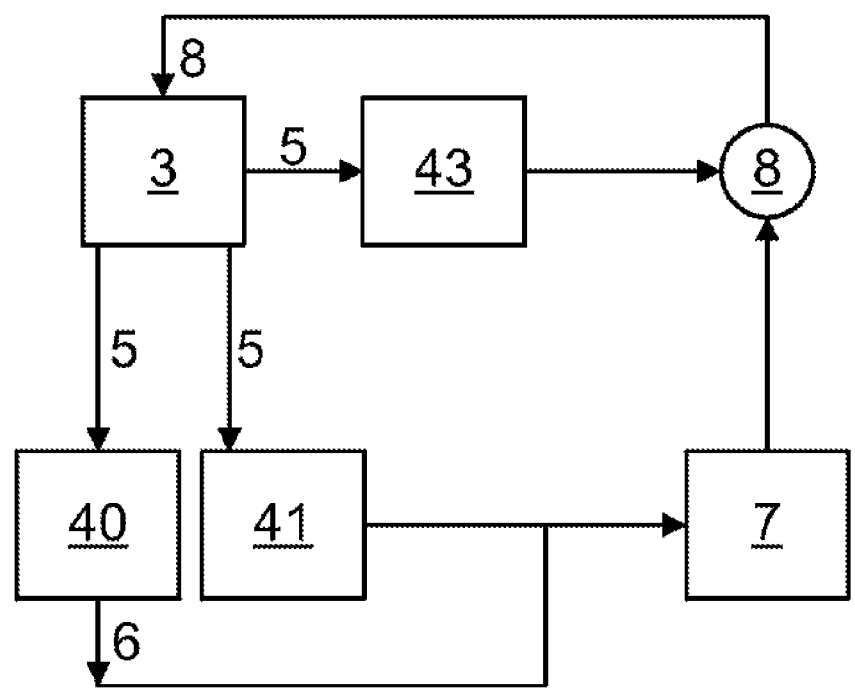
FIG. 5 represents a schematic diagram of the entirety of the procedure.

FIG. 1B illustrates step D of percolation of a liquid 8 through the substrate 2 of FIG. 1A in order to extract the hydrolytic enzymes 31 produced during step C in the form of a first leachate 5. The liquid 8 used for this enzyme extraction may be freshwater or a treated water (effluent) obtained from recycling leachates by anaerobic digestion, as illustrated in FIG. 5. This treated water may moreover be advantageously aerated before being re-used.

The substrate 2 may be used for 3 to 5 biostimulation cycles.

Once exhausted, it is withdrawn from the biostimulation reactor 3 and may advantageously be treated by aerobic treatment in order to obtain a stabilized compost 9, as illustrated in FIG. 1C.

Figure 2A:
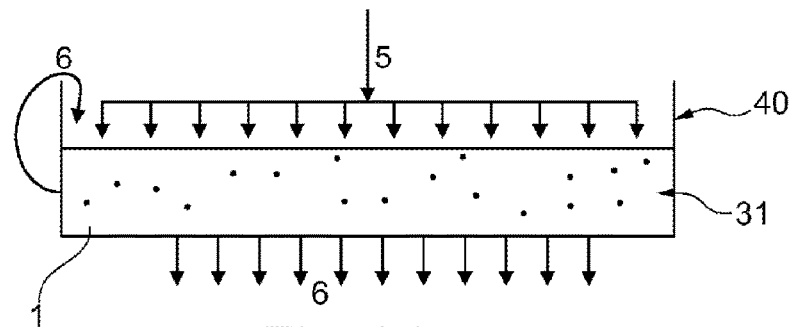
FIG. 2A represents a schematic diagram of a percolator 40 for the hydrolysis of a substrate to be treated according to a first embodiment of the process according to the invention.
Figure 2B:
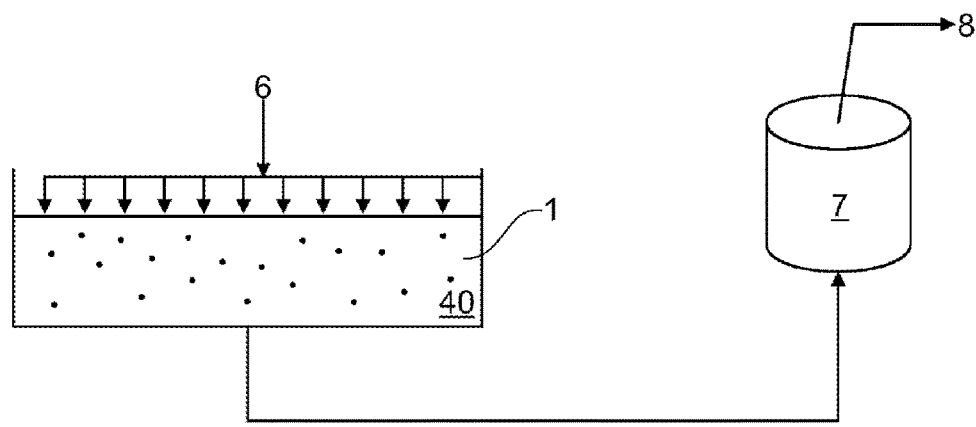
FIG. 2B represents a schematic diagram of the percolator 40 of FIG. 2A associated with a methanizer 7 for exploiting, by methanogenesis, the products resulting from the hydrolysis of the substrate to be treated originating from the percolator of FIG. 2A.
Figure 2C:
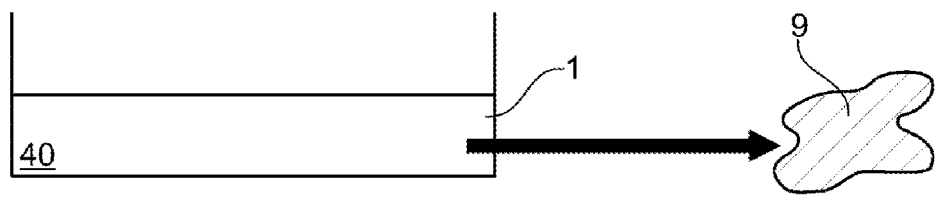
FIG. 2C represents a schematic diagram of the percolator 40 of FIGS. 2A and 2B for the aerobic treatment of the exhausted substrate in order to obtain a stabilized compost.

In FIGS. 2A to 2C, a percolator 40 is represented in which the hydrolysis of a substrate 1 to be treated occurs according to a first embodiment of the process according to the invention.

FIG. 2A illustrates the hydrolysis F as is, of the substrate 1 to be treated according to a first embodiment of the process according to the invention, which occurs in the solid phase, as follows:
- the first leachate 5 loaded with hydrolytic enzymes is injected into a percolator 40 containing the substrate to be treated,
- this first leachate 5 percolates through the substrate to be treated 1 to hydrolyze the organic matter of this substrate 1: at the outlet of the percolator 40 a second leachate 6 is then obtained, loaded with hydrolytic enzymes and with organic matter, which is recirculated into the percolator 40 until the hydrolyzable organic matter of the substrate 1 has in large part been hydrolyzed (substrate 1 exhausted).

Once this hydrolysis step has finished, this second leachate loaded with hydrolytic enzymes and with hydrolyzed organic matter is conveyed into a methanizer 7 for the production of methane, as illustrated in FIG. 2B. The treated water 8 at the outlet of the methanizer 7 is partially recycled upstream of the process according to the invention by being reinjected into the biostimulation reactor 3 (cf. FIG. 5 representing the procedure in its entirety).

Once exhausted, the substrate 1 is withdrawn from the percolator 40 and may advantageously be treated by aerobic treatment in order to obtain a stabilized compost 9, as illustrated in FIG. 2C.

Figure 3:
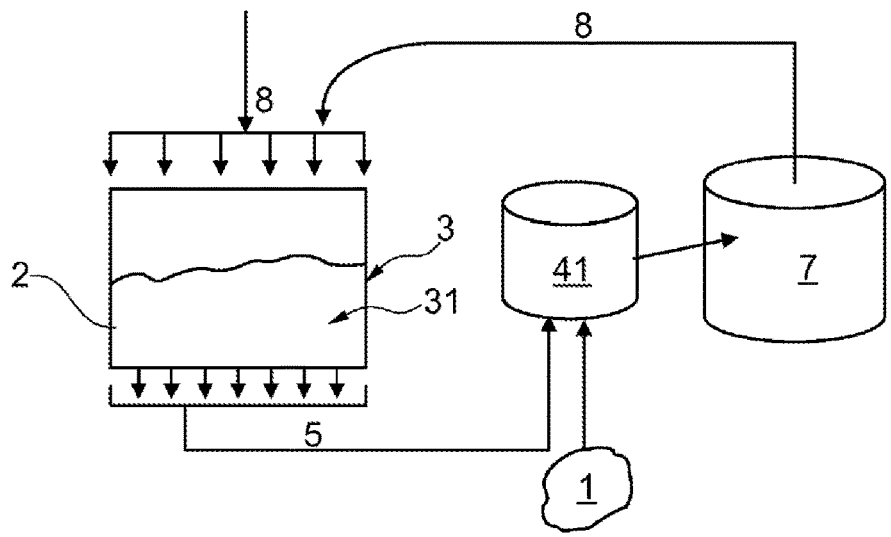
FIG. 3 represents a schematic diagram of a hydrolytic reactor 41 for carrying out the hydrolysis of a substrate to be treated according to a second embodiment of the process according to the invention.

A hydrolytic reactor 41 is represented in FIG. 3, in which the liquid-phase hydrolysis F of a substrate 1 to be treated occurs according to a second embodiment of the process according to the invention:
- the first leachate 5 loaded with hydrolytic enzymes originating from the biostimulation reactor 3 is injected into a hydrolytic reactor 41 upstream of a methanizer 7 in order to improve its performance in the context of a two-step treatment by anaerobic processes, such as, for example, the Biomet process;
- at the same time, the waste 1 to be treated is injected into this hydrolytic reactor 41.

The products obtained at the outlet of the reactor 41 are exploited downstream in the methanizer 7 by the production of biogas and the treated water 8 at the outlet of the methanizer 7 is partially recycled upstream of the process according to the invention by being reinjected into the biostimulation reactor 3, as illustrated in FIG. 5 which represents the procedure in its entirety.

Figure 4:
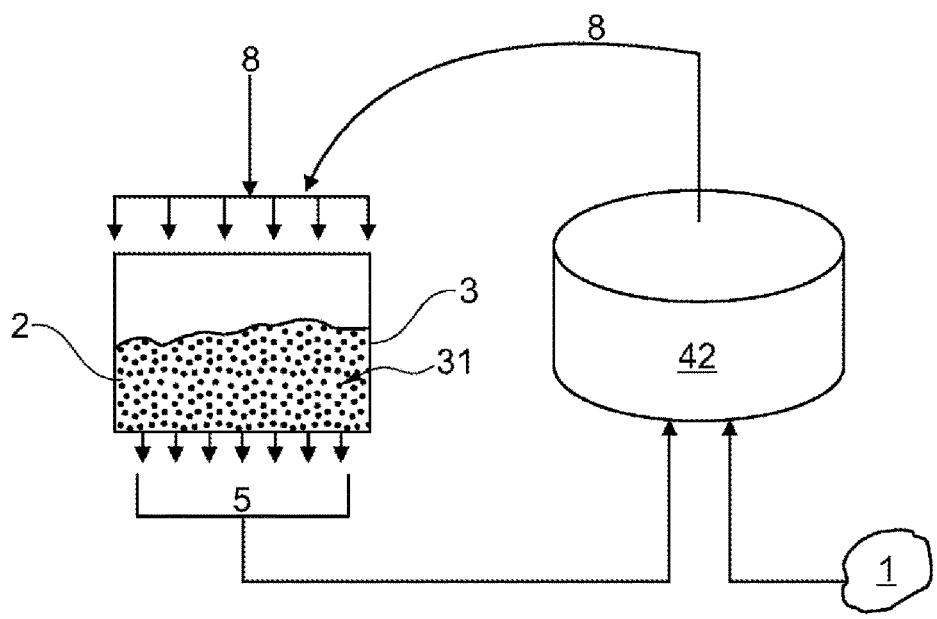
FIG. 4 represents a schematic diagram of an anaerobic digestion reactor 42 for carrying out the hydrolysis of a substrate to be treated according to a third embodiment of the process according to the invention.

An anaerobic digestion reactor 42 is represented in FIG. 4, in which the hydrolysis F of a substrate 1 to be treated occurs according to a third embodiment of the process according to the invention:
- the first leachate 5 loaded with hydrolytic enzymes originating from the biostimulation reactor 3 is injected into an anaerobic digestion reactor 42 in order to improve the performance of the process of the invention (by producing biogas especially);
- the steps of hydrolysis and of methanogenesis are carried out here in the same reactor 42 and correspond to anaerobic digestion;
- in the same way as for the first and second embodiments of the process according to the invention, the treated water 8 at the outlet of the reactor 42 is partially recycled upstream of the process according to the invention by being reinjected into the biostimulation reactor 3, as illustrated in FIG. 5 which represents the procedure in its entirety.

The following examples illustrate the invention without however limiting the scope thereof.

EXAMPLES

Various types of waste are hydrolyzed in an anaerobic digestion reactor 42 such as that illustrated in FIG. 4.

In the first example, this hydrolysis is carried out according to a conventional process, that is to say without addition of enzymes, whereas in the second example, commercial enzymes are added, produced by fermentation in liquid medium.

In the third example, the waste is hydrolyzed in accordance with the process according to the invention, by injecting, into the anaerobic digestion reactor 42, hydrolytic enzymes 31 originating from a biostimulation reactor associated with the anaerobic digestion reactor 42. These enzymes are produced in situ in the biostimulation reactor 3, in which the cycle of biostimulation of a substrate of household or agricultural waste (identical to or different from the waste to be treated) occurs according to the following operating conditions:
- residence time: 5 days
- moisture: 60%
- pH: 5
- temperature: 30° C.

At the end of the biostimulation step C, a liquid (for example fresh water) is percolated (step D) through the substrate in order to form a leachate enriched in hydrolytic enzymes, which is injected into the anaerobic reactor 42.

Products
- commercial enzymes, produced by fermentation in liquid medium, for example those sold by DSM under the trade name MethaPlus®.
- household waste substrate,
- agricultural waste substrate,
- these two types of waste being rich in lignocellulose, refractory organic matter which is not degraded in anaerobic conditions.

Tests

In the three examples described below, the hydrolysis performance of the waste to be treated is evaluated by measuring the gain in methane production (denoted by the acronym BMP, for biomethane potential).

The BMP analysis is carried out according to the recommendations described by Angelidaki et al[8]. (2009).

Test Results

Table 1 below collates the BMP measurements obtained for the three examples tested. These measurements are presented in table 1 in the form of an index relative to the conventional process, which is assigned an index of 100.

TABLE 1

| | BMP measurements | | |
| --- | --- | --- | --- |
| | Example 1 Conventional process | Example 2 Process employing commercial enzymes | Example 3 Process according to the invention |
| Household waste | 100 | 137 (gain of 37%/ conventional process) | 108 (gain of 8%/ conventional process) |
| Agricultural waste | 100 | 120 (gain of 20%/ conventional process) | 111 (gain of 11%/ conventional process) |

In order to carry out these measurements, the same volumes of enzymatic mixtures were added for the three examples. However, the compositions of these mixtures are not identical. Table 2 below presents the composition of the mixtures used in the processes of hydrolysis and of methanogenesis of examples 2 and 3. This composition is indicated in table 2 in enzymatic units/ml for 3 main enzymes:
- total cellulase or FPase,
- carboxymethylcellulase or CMCase,
- and β-glucosidase.

TABLE 2

| Composition of the mixture of commercial enzymes used in example 2 (in enzymatic units/ml) | | | Composition of the leachate originating from the biostimulation reactor 3, used in example 3 (in enzymatic units/ml) | | |
| --- | --- | --- | --- | --- | --- |
| FPase | CMCase | β-glucosidase | FPase | CMCase | β-glucosidase |
| 4 | 23 | 133 | 2 | 9 | 10 |

The results from table 1 certainly show that the BMP gain is greater, compared to the conventional process, if commercial enzymes are used (37/8=4.6 times greater for household waste, and 20/11=1.8 times greater for agricultural waste). However, in terms of enzymatic units, the differences are much greater between the mixture of commercial enzymes of example 2 and the leachate of example 3 according to the invention: they vary between 2 and 13.3 times more commercial enzymes.

This means that, for a comparable yield, it will be necessary to add more commercial enzymes than enzymes produced by biostimulation. It should be noted that the latter are produced under operating conditions which require fewer operational costs. The enzymatic mixtures from biostimulation may indeed contain additional enzymes which enable more effective hydrolysis.

REFERENCE LIST

[1] Kim S., C H. Kim *Production of cellulase enzymes during the solid-state fermentation of empty palm fruit bunch fiber*. Bioprocess and Biosystems Engineering 35: 61-67 (2012).
Rodriguez-Fernandez et al. (2012)
[2] Qian L.-C, S.-J. Fu, H.-M. Zhou, J.-Y. Sun, X.-Y. Weng *Optimization of fermentation parameters for β-glucosidase production by Aspergillus niger*. Journal of Animal and Veterinary Advances 11(5): 583-591 (2012).
[3] Rodriguez-Fernandez D. E., J. A Rodriguez-leon, J. C. de Carvalho, W. Sturm, C. R. Soccol *The behavior of kinetic parameters in production of pectinase and xylanase by solid-state fermentation*. Bioresource Technology 102: 10657-10662 (2011).
[4] Chahal D. S. *Solid state fermentation with Trichoderma reesei for cellulase production*. Applied and Environmental Biotechnology 49(1): 205-210 (1985).
[5] Kalogeris E., P. Christakopoulos, P. Katapodis, A. Alexiou, S. Vlachou, D. Kekos, B. J. Macris, *Production and characterization of cellulolytic enzymes from the thermophilic fungus Thermoascus aurantiacus under solid state cultivation of agricultural wastes*. Process Biochemistry 38: 1099-1104 (2003).
[6] Dave B. R., A. P. Sudhir, M. Pansuriya, D. P. Raykundaliya, R. B. Subramanian, *Utilization of Jatropha deoiled seed cake for production of cellulases under solid-state fermentation*. Bioprocess and Biosystems Engineering. Article in Press DOI 10.1007/s00449-012-0723-3 (2012).
[7] Acharya B. K., S. Mohana, R. Jog, J. Divecha, D. Madamwar, *Utilization of anaerobically treated distillery spent wash for production of cellulases under solid-state fermentation*. Journal of Environmental Management 91: 2019-2027 (2010).
[8] Angelidaki I., M. Alves, D. Bolzonella, L. Borzacconi, J. L. Campos, A. J. Guwy, S. Kalyuzhnyi, P. Jenicek, J. B. van Lier, *Defining the biomethane potential (BMP) of solid organic wastes and energy crops: a proposed protocol for batch assays*. Water Science and Technology 59(5): 927-934 (2009).

The invention claimed is:
1. A process for the treatment of a first, at least partially organic and at least partially solid, substrate, comprising:
   A. introduction of an initial volume of said first substrate to be treated into at least one hydrolysis reactor;
   B. introduction of an initial volume of second substrate into at least one biostimulation reactor;
   C. biostimulation of the second substrate contained in said biostimulation reactor by indigenous microorganisms and absent inoculated exogenous strains, under aerobic conditions, at a temperature of between 20° C. and 40° C., a pH of between 4 and 7, a moisture level of between 50% and 80% and a residence time of between 1 and 5 days, to ensure at least partial hydrolysis of the organic portion of said substrate and the in situ production of hydrolytic enzymes;
   D. percolation of a liquid through said volume of second substrate contained in said biostimulation reactor, in order to form a first leachate enriched in hydrolytic enzymes;
   E. injection of the first leachate enriched in hydrolytic enzymes into at least one hydrolysis reactor containing said first substrate to be treated; and
   F. hydrolysis of the first substrate at least partially by the first enriched leachate; wherein the succession of the steps C and D define a biostimulation cycle.

2. The process as claimed in claim 1, in which the hydrolytic enzymes are produced by filamentous fungi.

3. The process as claimed in claim 2, in which the filamentous fungi belong to the group consisting of the fungi *Trichoderma* sp., *Aspergillus* sp., *Pleurotus* sp., *Penicillium* sp., and *Fomitopsis* sp.

4. The process as claimed in claim 1, wherein the succession of the steps C and D defining a biostimulation cycle is repeated until the initial volume of second substrate in said biostimulation reactor is exhausted.

5. The process as claimed in claim 1, further comprising an additional step G of introduction of a new volume of second substrate into said biostimulation reactor when the initial volume of second substrate is exhausted.

6. The process as claimed in claim 1, wherein the hydrolysis step F is a step of hydrolysis which occurs essentially in the solid phase.

7. The process as claimed in claim 6, in which the step F of hydrolysis occurs in a percolator and comprises:
   percolation of said first leachate in the hydrolysis reactor through said first substrate to be treated, in order to obtain a second leachate enriched in hydrolytic enzymes and in organic matter; and
   reinjection of said second leachate into said hydrolysis reactor until the substrate is exhausted.

8. The process as claimed in claim 6, further comprising an additional step H of introduction of a new volume of first substrate into said hydrolysis reactor when the initial volume of first substrate is exhausted.

9. The process as claimed in claim 5, wherein the exhausted substrates, which originate from the biostimulation reactor and/or from the hydrolysis reactor when the hydrolysis step F occurs essentially in the solid phase, are treated by aerobic treatment with a view to obtaining a stabilized compost.

10. The process as claimed in claim 1, wherein the hydrolysis step F is a step of hydrolysis occurring essentially in the liquid phase in a hydrolytic reactor.

11. The process as claimed in claim 6, wherein the products resulting from the hydrolysis step F are exploited by a downstream step of methanogenesis in a methanizer for the production of biogas, at the end of which treated water is obtained.

12. The process as claimed in claim 1, in which the hydrolysis step F is carried out in an anaerobic digestion reactor for the treatment of the first substrate and the production of biogas, at the end of which treated water is obtained.

13. The process as claimed in claim 11, wherein the liquid percolating, during step D, in said biostimulation reactor for extracting the hydrolytic enzymes at least results from the treated water originating from the methanizer or from an anaerobic digester.

14. The process as claimed in claim 11, wherein the treated water originating from the methanizer or from an anaerobic digester are aerated before being recycled to be injected into said biostimulation reactor.

15. The process as claimed in claim 1, wherein the first leachate enriched in hydrolytic enzymes results from a single biostimulation reactor, and supplies a plurality of hydrolysis reactors.

16. The process as claimed in claim 1, in which the hydrolytic enzymes are produced by filamentous fungi, wherein the second substrate is a sample of the first substrate.

* * * * *